United States Patent [19]

Orts

[11] 4,163,011

[45] Jul. 31, 1979

[54] PEPTIDE COMPOUNDS AND COMPOSITIONS

[76] Inventor: Richard J. Orts, Rte. 3, Box 251C, Stillwater, Okla. 74074

[21] Appl. No.: 937,300

[22] Filed: Aug. 28, 1978

[51] Int. Cl.² .................... C07C 103/52; A61K 37/00
[52] U.S. Cl. .................... 260/112.5 R; 260/112.5 LH; 424/177
[58] Field of Search .............. 260/112.5 R, 112.5 LH; 424/177

[56] References Cited

PUBLICATIONS

Pettit, Synthetic Peptides, vol. 4, pp. 186, 187.

*Primary Examiner*—Delbert R. Phillips
*Attorney, Agent, or Firm*—Robert A. Armitage

[57] ABSTRACT

The present invention relates to a bovine pineal tripeptide, exhibiting the amino acid sequence:

Thr—Ser—Lys wherein Thr is threonine, Ser is serine and Lys is lysine, and pharmacologically acceptable carboxy and acid addition salts thereof. The invention provides for the isolation of this tripeptide substantially free from all other pineal gland substances, including the various pharmacologically active pineal indoles and polypeptides. Also provided are methods for using this bovine pineal tripeptide for antifertility purposes.

2 Claims, No Drawings

PEPTIDE COMPOUNDS AND COMPOSITIONS

BACKGROUND OF THE INVENTION

I. Field of the Invention

The present invention provides novel organic compounds, useful for antifertility purposes. Particularly, the present invention provides a novel polypeptide isolated from the mammalian pineal gland. More particularly, there is provided a novel bovine pineal tripeptide and salts thereof with antigonadotrophic activity.

Also provided by the present invention are novel methods for isolation of a bovine pineal tripeptide from the bovine pineal gland.

Gonadotropins are a class of substances which stimulate male and female gonads, thus ordinarily representing profertility or fertility-maintaining agents. The gonadotropins include luteinizing hormone (LH) which stimulates ovulation and post-ovulatory progesterone production in the female ovaries. Another gonadotropin, follicle stimulating hormone (FSH), is a secondary pituitary hormone which stimulates the pre-ovulatory maturation of the Graafian follicles of the ovary, thus encouraging estrogen production therein. Thus, both LH and FSH stimulate estrogen or progesterone production and release from the ovaries, and are thereby essential for the establishment and maintenance of fertility.

In the male, FSH supports the germinal cells of the testes, while LH stimulates testosterone production. Hence these gonadotropins are essential to spermatogenesis and thus fertility in the male.

In addition to LH and FSH an hormonal substance from the hypothalamus, gonadotropin releasing hormone (GnRH), is known to be an endogenous agent for the stimulation of LH and FSH release. This substance is alternately known as LH-RH (luteinizing hormone releasing hormone) or LRF (luteinizing hormone releasing factor).

Because the gonadotropins are essential to the maintenance of fertility in both the male and the female, antigonadotrophic substances have been sought for use as antifertility or fertility-suppressing agents.

One fruitful source of antigonadotrophic substances has been the mammalian pineal gland, from which two broad classes of antigonadotrophic compounds have been isolated: polypeptides and indoles. With regard to the latter class, the most widely examined antigonadotrophic substance is melatonin, which, inter alia, reduces the effects of MSH (melanocyte stimulating hormone). Other pineal-derived antigonadotrophic indoles include serotonin, 5-hydroxytryptophol, 5-methoxytroptophol, and N-acetylserotonin.

With regard to pineal antigonadotrophic polypeptides, one important such substance is arginine vasotocin, which was first isolated by Milcu, S.M., et al., Endocrinology 72:563–566 (1963). For the structure of arginine vasotocin, see Cheesman, Biochim. Biophys. Acta. 207:247–253 (1970) and German offenlegungsschrift 2,739,492, published Mar. 3, 1978 (Derwent Farmdoc CPI No. 18163A).

Various other pineal antigonadotrophic polypepetides have been reported by various workers. For a brief review of reports of such polypepetides, see Table 3 (pages 164–166 of Reiter, Russell J., et al., "Pineal Antigonadotrophic Substances: Polypeptides and Indoles", Life Sciences 21:159–172 (1977).

A further review of pineal antigonadotrophic polypeptides, particularly a disclosure of certain uncharacterized (e.g., no amino acid content or amino acid sequence) polypepetides is provided by Orts, R.J., et al., "Antifertility Properties of Bovine Pineal Extracts: Reduction of Ovulation and Pre-Ovulatory Luteinizing Hormone in the Rat", Acta. Endocrinologica. 85:255–234 (1977), and Orts, R.G., "Reduction of Serum LH and Testosterone in Male Rats by a Partially Purified Bovine Pineal Extract", Biology of Reproduction 16:249–254 (1977).

II. Prior Art

The existence of pineal antigonadotrophic polypeptides and their antifertility properties is known in the art. See Orts, R.J., et al., "Antifertility Properties of Bovine Pineal Extracts: Reduction of Ovulation and Pre-Ovulatory Luteinizing Hormone in the Rat", Acta Endrocrinologica. 85:225–234 (1977), and Orts, R.J., "Reduction of Serum LH and Testosterone in Male Rats by a Partially Purified Bovine Pineal Extract", Biology of Reproduction 16:249–254 (1977). Moreover, a general review of both polypeptide-type and indole-type pineal anti-genadotrophic substances is provided by Reiter, Russell J., et al., "Pineal Antigonadotrophic Substances: Polypeptides and Indoles", Life Sciences 21:159–172 (1977), cited above.

SUMMARY OF THE INVENTION

The present invention provides novel compositions of matter. In particular, the present invention provides a novel composition of matter consisting essentially of a pineal antigonadotrophic polypeptide.

The present invention further provides novel methods for the isolation of a pineal antigonadotrophic polypeptide substantially free from all other pineal-derived substances.

Most particularly, the present invention provides:

(a) a bovine pineal antigonadotrophic polypeptide, being substantially free from all other pineal-derived substances, which is characterized by the amino acid sequence: threonine-serine-lysine; and (b) the pharmacologically acceptable carboxy salts and acid addition salts of the tripeptide characterized by the amino acid sequence: threonine-serine-lysine.

The carboxyl-terminated residue of the bovine pineal antiqonatrophic tripeptide is lysine and the N-terminus is threonine.

The bovine pineal antigonadotrophic tripeptide of the present invention is prepared by a novel process, described in detail by Example 1 hereafter, which comprises a further aspect of the present invention.

Because of the purity and homogeneity of the bovine pineal antigonadotrophic tripeptide in accordance with the present invention, it represents a surprisingly and unexpectedly improved antifertility agent, as compared with previously known bovine pineal antigonadotrophic polypeptide compositions. Thus, while the novel bovine pineal antigonadotrophic tripeptide is useful for the same antigonadotrophic (therefore antifertility) purposes as the prior art compositions, smaller dosages and fewer untoward side effects are evidenced when the novel compositions are employed for pharmaceutical purposes.

Even more strikingly, the provision of a single and strikingly active tripeptide in accordance with the present invention advantageously permits the chemical synthesis of the tripeptide from its amino acid constituents. Such a chemical synthesis is readily accomplished by methods known in the art. Thus, the present invention permits the induction of antifertility effects of the bovine pineal antigonadotrophic polypeptide factors to be made widely available without reliance on the comparatively tedious and uneconomic procedure of extraction from mammalian sources.

The novel pineal antigonadotrophic tripeptides in accordance with the present invention are employed whenever the induction of an antigonadotrophic effect is indicated. While, as indicated above, such antigonadotrophic effects are typically antifertility effects, the present invention also provides for antigonadotrophic effects which are essentially pro-fertility (e.g., estrous regulation in non-primates), or merely secondarily related to fertility (e.g., management of steroid-supported carcinoma).

The bovine pineal antigonadotrophic tripeptides of the present invention are useful in both humans and valuable domestic animals, including zoological specimens. The dosages employed are those wherein effective suppression of gonadotrophic hormones is achieved. The actual suppression of the gonadotropins is readily determined in any patient or animal by measuring changes in serum levels of these hormones, by known (e.g., radioimmunoassay) techniques. While the effective dose for a particular patient or an animal will depend upon the species, sex, age, indication, and condition of the subject, ordinarily an acute dosage of between 1 and 1,000 ng/kg, intravenously, is effective to suppress gonadotrophic activity. In those indications where sustained depression of gonadotrophic activity is required, subsequent and periodic doses of the bovine pineal antigonadotrophic tripeptides are administered. The precise regimen for administration can be readily adjusted for any patient or animal based upon serum levels of gonadotrophic hormones or subjective indices of response.

The pineal antigonadotrophic tripeptides are administered by any convenient route of administration (e.g., subcutaneously, intramuscularly, vaginally bucally, intranasally, or orally) with equivalent dosages to those referred to above for intravenous administration. Equivalent dosages refer to those dosages by such other routes of administration as provides equivalent systemic (e.g., serum) levels of the tripeptide and equivalent suppression of gonadotrophic hormones. Accordingly routes of administration other than intravenous ordinarily require substantially increased dosages of the tripeptide. For example, the intramuscular dose will range from 2 to 10 times the intravenous dose, while the oral dose will in most cases be significantly higher than the intramuscular dose. In any case the appropriate equivalent dosage is determined by patient or animal response (i.e., gonadotropin suppression).

For the various routes of administration, conventional dosage forms are employed. Accordingly, sterile solutions are employed where parenteral administration is selected, while suppositories are conveniently used when vaginal or rectal routes of administration are selected. When oral routes of administraton are selected, enteric-coated tablets or capsules will represent a preferred dosage form in those cases where variations in gastric pH would create unpredictability in the rate of tripeptide absorbed versus the rate of gastric hydrolysis.

Regarding the indications for use of the novel bovine pineal tripeptides in mammalian males, administration of an antigonadotrophic amount results in a significant reduction of or cessation of spermatogenesis, thereby abolishing male fertility. Since the effect on spermatogenesis is accompanied by a decrease in testosterone levels, supplemental androgenic steroid therapy may be indicated to restore libido. However, in those patients and animals where diminished libido and the associated behavioral changes are a desirable additional effect of the tripeptide, no additional androgenic steroid therapy is indicated. Patients within the latter category would include those in certain institutions (e.g., prisons and mental hospitals), while animals within the latter category would include canine and feline species where the effect of the tripeptide would be tantamount to a reversible castration.

Since an effective male antispermatogenic or antifertility agent requires that drug be delivered chronically, one preferred method of administration for this and other chronic indications is by a prolonged-release formulation or a prolonged-release device. Many such devices, e.g., comprising a drug reservoir surrounded by a controlled release rate membrane, are applicable for the chronic and controlled release of the novel bovine pineal antigonadotrophic polypeptides of the present invention. A second preferred method for chronic administration is in the food or feed of the patient or animal being treated.

In female mammals, suppression of gonadotrophic hormones is effective to (1) prevent ovulation, and (2) reverse any CL progesterone-supported pregnancy. With regard to the first of these uses, suppression of ovulation in humans is accomplished by administering the novel pineal antigonadotrophic tripeptide from the time of menses to about three weeks after the initiation of the menses. In estrous-cycling animals the novel pineal antigonadotrophic tripeptides are administered chronically to prevent ovulation.

With regard to the reversal of CL-supported pregnancy, in those animals where a functioning corpus luteum (CL) is required for the maintenance of pregnancy, the administration of the novel pineal antigonadotrophic tripeptide after conception will either prevent implantation or reverse fetal implants, thereby reversing early pregnancy. For this purpose, the pineal antigonadotrophic tripeptide is given, for example, in humans over several days, beginning prior to the next anticipated menses. In non-primates the time initiation of treatment ranges from immediately post-conception to midterm and continues over several days.

In estrous-cycling mammals, the novel pineal antigonatrophic tripeptide is useful in the regulation or synchronization of the estrous cycle, by regression of the corpus luteum. For this purpose, the timing during the estrous cycle of the pineal antigonadotrophic tripeptide administration is similar to that employed by other corpus luteum-regressing or luteolytic agents (e.g., the prostaglandins). Thus in the polyestrous animal the treatment is continued for about one-half of a single cycling period and ovulation will then occur at a predetermined time thereafter. In addition to the pro-fertility effects of estrous regulation, mammals infertile because of a persistent corpus luteum may also be brought into estrus and successfully bred after treatment with the pineal antigonadotrophic tripeptides of the present invention.

In addition to the various fertility-related indications recited above, certain other non-fertility uses of the pineal antigonadotrophic tripeptides include the treatment of precocial puberty, and steroid-supported carcinoma. These disease states, which often require the removal of the gonadotropin-producing gland (pituitary) or the gonads themselves, are thus non-surgically treated in accordance with the present invention. In those cases where sustained supression of gonadal function is desired (e.g., steroid-supported carcinoma of the breast or prostrate), the prolonged-release formulations or devices described above are employed.

As indicated above, any of the various pharmacologically acceptable carboxy salts or acid addition salts of Thr-Ser-Lys are used in accordance with the present invention. These salts are respectively prepared from the tripeptide of Example 1, below, by mixture with a dilute solution of the base or acid corresponding to the carboxy or acid addition salt to be prepared. Thereafter the salts are recovered in solid form by conventional techniques, i.e., concentration under reduced pressure.

Among the pharmacologically acceptable carboxy salts in accordance with the present invention are various metal salts, including alkali and alkaline metal salts, and heavy metal salts. Also, amine salts, including primary and secondary and tertiary amine salts, are included, as well as the quaternary ammonium salts.

With regard to the acid addition salts, there are included conventionally employed acid salts of pharmaceuticals, such as the hydrochloride and hydrobromide salts. As is apparent, however, from the above list, suitable salts for use in accordance with the present invention are characterized only by the absence of substantial toxicity and suitability for pharmaceutical formulation.

DESCRIPTION OF THE PREFERRED EMBODIMENTS

EXAMPLE 1

Threonine-serine-lysine from the bovine pineal gland

A. Fresh bovine pineal glands (120 g) are lyophilized and thereafter homogenized in acetone (100 ml) with stirring for 4 hr at 4° C. The resulting residue is then filtered, washed with acetone (20 ml) and concentrated under reduced pressure at 55° C. The resulting powder is then dispersed in 2.0 N acetic acid (30 ml) and stirred for one hr at ambient temperature. Thereafter the resulting acetic acid mixture is centrifuged at 16,300 g for 2 hr and the supernatant collected and lyophilized. This residue is then dissolved in glacial acetic acid (20 ml), stirred for 45 min at ambient temperature, and centrifuged at 12,000 g for 30 min. Thereafter the supernatant is diluted with distilled water (50 ml) and lyophilized. The resulting residue is then dissolved in 1.0 N acetic acid (10 ml) and centrifuged at 48,200 g for one hr.

B. Following the above mild acid extractions, the final supernatant of Part A is lyophilized and the residue dissolved in 0.06 M acetic acid (3 ml of acid per 100 g of residue), pH 3.0, and placed on a column (30 cm×1.5 cm) of analytical grade polystyrene cation exchange resin, Dowex 50[H+], prewashed successively with 2 N sodium hydroxide, distilled water, 2 N hydrochloric acid, and distilled water. Elution successively with water (75 ml), 0.2 M aqueous pyridine (pH 4.0, 75 ml), 0.2 M pyridine (pH 5.0, 150 ml) and 1 M pyridine (pH 7.5-8.5, 75 ml) yields in the 1 M pyridine fractions a product which is collected and lyophilized. The resulting residue is then dissolved in 1% aqueous ammonium bicarbonate ($NH_4HCO_3$) and placed on a column (80 cm×1.5 cm) of cross-linked dextran gel (Sephadex G25 Fine), equilibrated with 1% aqueous ammonium bicarbonate at ambient temperature. Elution of a column with 1% aqueous ammonium bicarbonate at a flow rate of 45 ml/hr, collecting 4 ml fractions, yields a crude product A in fractions 30-36. This crude product is then lyophilized and the residue dissolved in water.

C. The aqueous mixture of Part B is then further purified by vertical flow paper electrophoresis. The crude product in the aqueous mixture is spotted on the paper and run for 30 min at 3,000 v in a mixture of pyridine, acetic acid, and water (100:4:900), pH 6.5. In fraction 4 (of 16 fractions running from cathode to anode), the $R_L$ is 0.77-0.83 wherein $R_L$ is the ratio of the migration distance of the fraction of interest to that of lysine during the vertical paper electrophoresis. This fraction is then eluted with water and subsequently lyophilized.

D. The residue of Part C is then dissolved in water and further purified by descending paper chromatography for 10 hr using butanol, acetic acid, and water (5:1:4) as a solvent system and 3 mm Whatman chromatography paper. From this chromatogram, a fraction whose $R_f$ is 0.15-0.22 is eluted and lyophilized. The resulting residue provides the bovine pineal antigonadotrophic tripeptide threonine-serine-lysine substantially free from all other pineal-derived substances.

E. The amino acid sequence of the tripeptide of Part D is determined by the Edman degradation procedure described by Salnikow, J., et al., J. Biol. Chem. 248:1480.

EXAMPLE 2

Effects of threonine-serine-lysine on mammalian species

A. Compensatory Ovarian Hypertrophy (COH) is an effect in standard laboratory (mammalian) animals for assessing antigonadotrophic activity by determining the increase in weight of the remaining gonad after unilateral gonadectomy. Procedures for COH measurement in female rats are described in Ramirez, V.D., et al., Endocrinology 95:475 (1974). According to these known procedures threonine-serine-lysine, prepared in Example 1, is administered intraperitoneally to adult female mice on the same day as a unilateral ovariectomy is performed. On day 5, both experimental and control animals are sacrificed and mean ovarian weights are obtained. The results of this study, reported in Table I below, indicate that the COH or compensatory ovarian hypertrophy (i.e., the difference in ovarian weights as a percentage of the weight of the gonadectomized ovary) is reduced in a dose-dependent manner in animals treated with the threonine-serine-lysine.

TABLE I

| Reduction of Compensatory Ovarian Hypertrophy | |
|---|---|
| Dose (ng) | COH ($\pm$ SE) |
| Control | 45.5 $\pm$ 5.3 |
| 186.1 | 34.6 $\pm$ 6.8 |
| 372.2 | 11.1 $\pm$ 15.1 |

B. The effect of threonine-serine-lysine on serum concentrations of FSH in the adult female rat is measured 24 hr after intraperitoneal injection of threonine-serine-lysine to unilaterally ovariectomized mice. On day 5 after injection, the animals were sacrificed and ovarian weights recorded There are then determined compensatory ovarian hypertrophy (5 days after treatment) as well as the serum FSH (24 hr after treatment). The results of this study are reported in Table II below.

TABLE II

Effect of Threonine-Serine-Lysine on Compensatory Ovarian Hypertrophy and Serum FSH in Female Mice

| No. of animals | Dose (ng) | COH (± SE) | Serum FSH (± SE) ng/ml |
|---|---|---|---|
| 6 | Control | 29.7 ± 8.4 | 296.8 ± 375 |
| 8 | 35.1 | 12.6 ± 10.9 | 254.4 ± 88.7 |
| 8 | 70.3 | 21.9 ± 8.0 | 377.0 ± 56.9 |
| 8 | 175.7 | 12.9 ± 5.0 | 165.0 ± 22.5 |
| 8 | 351.7 | 21.1 ± 7.8 | 179.0 ± 60.9 |

C. The antifertility effects of threonine-serine-lysine on the male rat are measured by their ability to inhibit GnRH-or gonadotropin releasing hormone-induced rise in FSH when threonine-serine-lysine is administered intravenously. In this test, both control and tripeptide-treated animals received GnRH in a phosphate buffered saline solution, followed by the administration of the tripeptide in the same buffer. Five animals each were in one control and three tripeptide-treated groups, with the results reported in Table III indicating FSH suppression.

TABLE III

Reduction of Serum FSH in GnRH-treated Male by Threonine-Serine-Lysine

| Dose (ng) | Mean concentration of plasma FSH (ng/ml ± SE) ng/ml | | | |
|---|---|---|---|---|
| | 0 min | 15 min | 30 min | 60 min |
| Control | 362.5 ± 20.7 | 1753.4 ± 450.6 | 1701.6 ± 720.6 | 247.8 ± 14.0 |
| 1.48 | 302.2 ± 26.2 | 338.4 ± 38.8 | 592.5 ± 217.6 | 586.5 ± 301.3 |
| 14.8 | 45.6 ± 52.3 | 402.9 ± 117.7 | 472.7 ± 76.9 | 684.5 ± 142.0 |
| 148 | 43.9 ± 85.6 | 646.1 ± 198.0 | 1407.8 ± 499.6 | 1279.6 ± 180.8 |

I claim:

1. A bovine pineal antigonadotrophic tripeptide, being substantially free from all other pineal-derived substances, which is characterized by the amino acid sequence: Threonine-serine-lysine.

2. The pharmacologically acceptable carboxy salts and acid addition salts of the tripeptide characterized by the amino acid sequence: Threonine-serine-lysine.

* * * * *

UNITED STATES PATENT OFFICE
CERTIFICATE OF CORRECTION

Patent No. 4,163,011  Dated 31 July 1979

Inventor(s) Richard J. Orts

It is certified that error appears in the above-identified patent and that said Letters Patent are hereby corrected as shown below:

Column 2, line 46, "antiqonatrophic" should read -- antigonatrophic --;
Column 3, line 40, "vaginally bucally," should read -- vaginally, bucally, --;
Column 7, line 17, "29.7 ± 8.4" should read -- 29.7 ± 3.4 --.

Signed and Sealed this

Twenty-second Day of July 1980

[SEAL]

Attest:

SIDNEY A. DIAMOND

Attesting Officer  Commissioner of Patents and Trademarks